United States Patent [19]

Vopilkin et al.

[11] 3,968,680

[45] July 13, 1976

[54] WIDE-BAND ULTRASONIC TRANSDUCER AND ITS USES

[76] Inventors: Alexeli Kharitonovich Vopilkin, ulitsa Vorovskogo, 20, kv. 9; Igor Nikolaevich Ermolov, Ryazansky prospekt, 19, kv. 50; Vladimir Ivanovich Ryzhov-Nikonov, Simonovsky val, 13, kv. 26, all of Moscow; Valery Ivanovich Ivanov, Bolnichny pereulok, 3, kv. 1, Podolsk Moskovskoi oblasti; Vladimir Izidorovich Ryk, pereulok Aksakova, 18, kv. 14, Moscow; Viktor Vasilievich Rakhmanov, Spartakovskaya ulitsa, 8, kv. 1, Kaliningrad Moskovskoi oblasti; Vladimir Dmitrievich Korolev, Volkov pereulok, 9, kv. 41; Petr Yakovlevich Krasinsky, Malaya Filevskaya ulitsa, 40, kv. 31, both of Moscow, all of U.S.S.R.

[22] Filed: Feb. 25, 1975

[21] Appl. No.: 552,782

[52] U.S. Cl. ............................... 73/67.8 R
[51] Int. Cl.² ............................. G01N 29/00
[58] Field of Search ........... 73/67.5 R, 67.7, 67.8 R, 73/71.5; 310/9.6

[56] References Cited
UNITED STATES PATENTS 2,447,061  8/1948  Franklin .................. 310/9.6 X
2,485,722  10/1949  Erwin .................... 310/9.6 X
2,486,916  11/1949  Bottom .................. 310/9.6

Primary Examiner—James J. Gill
Attorney, Agent, or Firm—Haseltine, Lake & Waters

[57] ABSTRACT

A wide-band ultrasonic transducer comprising: a body of revolution; at least two electrodes connected to the body of revolution; the body of revolution being made of a material having piezoelectric properties; the body of revolution having one flat end face surface, whereas its other end face surface, opposite to the flat end face surface, is profiled. The profile of the profiled end face surface of the body of revolution is made in accordance with the following relationship:

$$h' = -\rho \cdot h \cdot k(f)$$

where
$\rho$ is the radial coordinate;
$h$ is the thickness of the transducer, corresponding to the radical coordinate;
$k(f)$ is the frequency characteristic of the transducer within the operating frequency range; and
$h'$ is the derivative of the transducer thickness with respect to the radial coordinate.

The electrodes are applied onto the flat end face surface and the profiled end face surface of the body of revolution.

16 Claims, 29 Drawing Figures

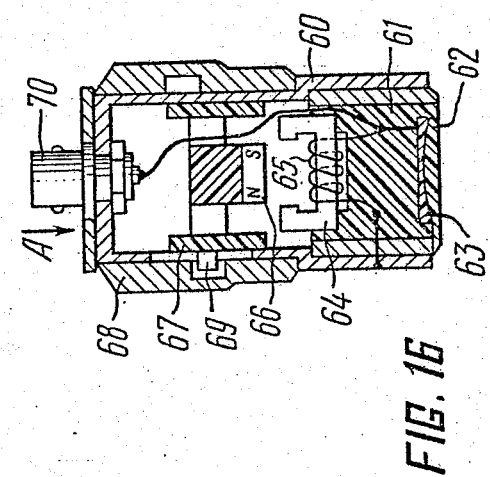
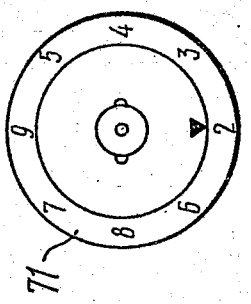
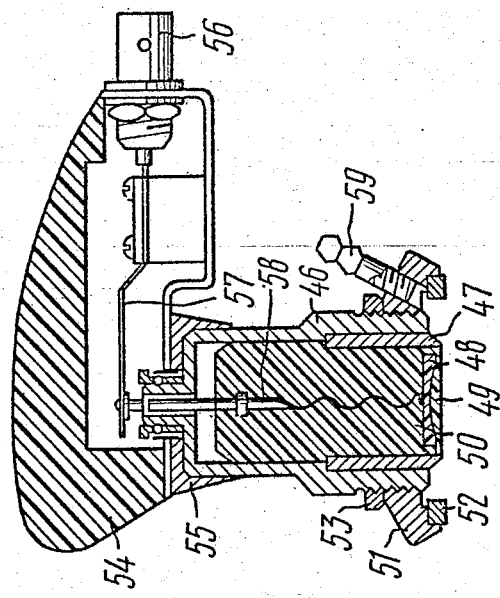

3,968,680

WIDE-BAND ULTRASONIC TRANSDUCER AND ITS USES

The present invention relates to ultrasonic measuring equipment and, more particularly, to devices for nondestructive ultrasonic flaw detection and wide-band ultrasonic transducers.

Work on methods and means for ultrasonic measurements often involves the task of emitting and receiving ultrasonic oscillations within a wide frequency range. This especially applies to work with materials having different frequency-dependent attenuations. At present wide-band ultrasonic transducers operating within a sufficiently broad frequency range incorporate mechanically and electrically damped flat-parallel converters.

The foregoing converters are disadvantageous in that they are marked by great non-uniformity of frequency characteristics and a narrow frequency pass band, which results in low reliability and accuracy of checking.

The selection of matching transition layers between a wide-band ultrasonic transducer and an article being checked makes it possible to somewhat broaden the frequency pass band, yet the non-uniformity of the frequency characteristic remains; in checking articles having different acoustic properties this results in an unstable frequency characteristic. Besides, the available frequency pass band does not make it possible to carry out a number of nondestructive ultrasonic checking methods, in particular, ultrasonic structurometry, etc.

There are also known wide-band ultrasonic transducers with a variable resonance thickness, which transducers are constructed in the form of a single-taper wedge. Although having a broad frequency pass band, this type of transducer is marked by considerable non-uniformity of the frequency characteristic, the non-matching of the geometrical and acoustical axes and low sensitivity.

There are further known wide-band ultrasonic transducers comprising a body of revolution having flat end face surfaces and electrodes applied onto said end face surfaces.

The latter transducers also suffer from the above-mentioned disadvantages.

The foregoing wide-band ultrasonic transducers are employed in ultrasonic measuring and testing heads and in devices for nondestructive ultrasonic checking, for example, for measuring the thickness of articles, flaw detection, studies in the structure of materials, etc.

The known ultrasonic testing heads comprise a housing, a damper, a piezoelement and a protector. In these heads the piezoelement is constructed as a body of revolution with flat-parallel emitting surfaces, whereas the protector is made as a quarter-wave flat-parallel layer. In the known testing heads the quarter-wave protector matches acoustic resistances of the transducer and an article being checked in a narrow frequency range. Between the protector and the article being checked there is also a layer of contact fluid. As the testing head moves across the surface of the article, the thickness of the contact fluid layer may vary within broad limits, so the emission and reception resonance frequency of the transducer also changes. This leads to mismatching of the protector, considerable variations in the amplitude of the received signal and distortions in the frequency characteristic.

There are also known ultrasonic testing heads similar to those described above, wherein the ultrasonic oscillation frequency is trimmed with the aid of an inductance coil.

A disadvantage of the known ultrasonic testing heads is the impossibility of emitting and receiving ultrasonic oscillations within a broad frequency range. While switching to another frequency, one has to use another testing head with another inductance coil.

There are known devices for nondestructive checking, intended for detecting flaws and their nature. The operation of such devices is based upon the spectral analysis of echo signals reflected from flaws.

The known devices under review comprise a main pulse generator with a broad frequency range, a converter of electrical oscillations into ultrasonic oscillations and vice versa, connected to an output of said generator, a wide-band receiving unit connected to the converter, and a signal processing unit.

In said devices the function of the converter is performed by plane-parallel damped piezoelements. The piezo-elements have a directional diagram comprising a major lobe and minor lobes.

A disadvantage of the known devices under review is the fact that the presence in the directional diagram of minor lobes in many cases accounts for a high level of noise in the form of ghost echo signals which are at times difficult to get rid of.

It is an object of the present invention to provide an ultrasonic transducer with a wide pass band, which would make it possible to have a frequency characteristic with a preselected relationship between variations in the amplitude and frequency, so that the amplitude may be, for example, uniform, linearly increasing, increasing in proportion to the square of the frequency, etc.

The foregoing object is attained by providing a wide-band ultrasonic transducer comprising a body of revolution made of a material having piezoelectric properties, and at least two electrodes applied onto the end face surfaces of the body of revolution, one of which surfaces is flat, whereas the other is profiled in accordance with the following relationship:

$$h' = -\rho \cdot h \cdot k(f)$$

where
$\rho$ is the radial coordinate;
$h$ is the thickness of the transducer, corresponding to the radial coordinate;
$k(f)$ is the frequency characteristic of the transducer;
$h'$ is the derivative of the transducer thickness with respect to the radial coordinate.

It is expedient that the end face surface profile of the body of revolution for conversion with a uniform frequency characteristic within the operating frequency range be made in accordance with the relationship:

$$h = e^{-a\rho^2} + c$$

where $a$ and $c$ are constant values determined by the operating frequency range.

In the case of a linearly rising frequency characteristic of the transducer in the operating frequency range, the end face surface must be profiled according to the relationship:

$$h = c - a'p^2$$

If the frequency characteristic of the transducer rises in proportion to the square of the frequency within the operating frequency range, it is advisable that the end face surface should be profiled according to this relationship:

$$h = c - e^{-ap}$$

It is also expedient that the proposed wide-band ultrasonic transducer be utilized in a testing head for nondestructive ultrasonic checking, which head comprises, apart from said transducer, a housing, a damper arranged in said housing, a protector connected to the wide-band ultrasonic transducer, in which head the wide-band ultrasonic transducer is constructed, in accordance with the invention, like one of the foregoing embodiments and faces the damper with its flat end face surface, the surface of the protector, facing the wide-band ultrasonic transducer, being congruent with its profiled end face surface.

It is advisable that said testing head be provided with a ferromagnetic core having an inductance coil wound therearound, which coil forms, together with the wide-band ultrasonic transducer, an oscillatory circuit, there being inserted into the ferromagnetic core gap a permanent magnet adapted for axial movement.

Likewise, it is expedient that an ultrasonic checking device comprising a generator of probing frequency-modulated oscillations, a wide-band ultrasonic transducer connected to an output of the generator of probing frequency-modulated oscillations, a wide-band receiving unit connected to the wide-band ultrasonic transducer, a signal processing unit connected to said wide-band receiving unit, include, in accordance with the invention, an intrapulse frequency modulation oscillator connected to the wide-band ulstrasonic transducer, and a smoothing filter placed between said wide-band ultrasonic transducer and the signal processing unit, said wide-band ultrasonic transducer being constructed according to one of the foregoing embodiments thereof.

Other objects and advantages of the present invention will become more apparent from the following detailed description of preferred embodiments thereof taken in conjunction with the accompanying drawings, wherein:

FIGS. 1a, b, c, d, e, and f represent different frequency characteristics of a wide-band ultrasonic transducer according to the invention;

Figure 13:
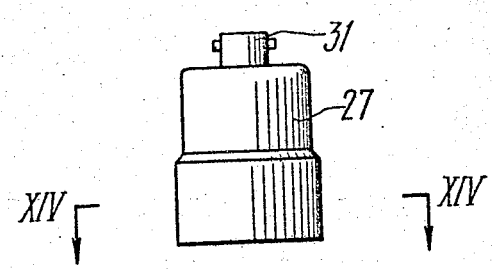
FIG. 13 is a general view of a testing head according to the invention.
Figure 14A:
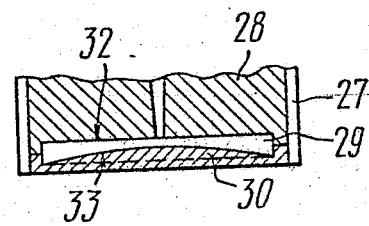
Figure 17:
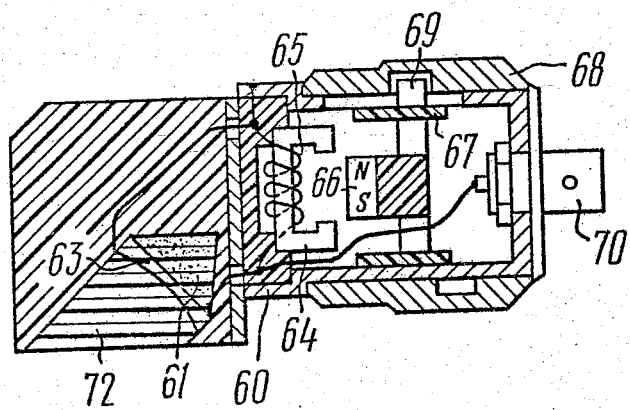
Figure 18:
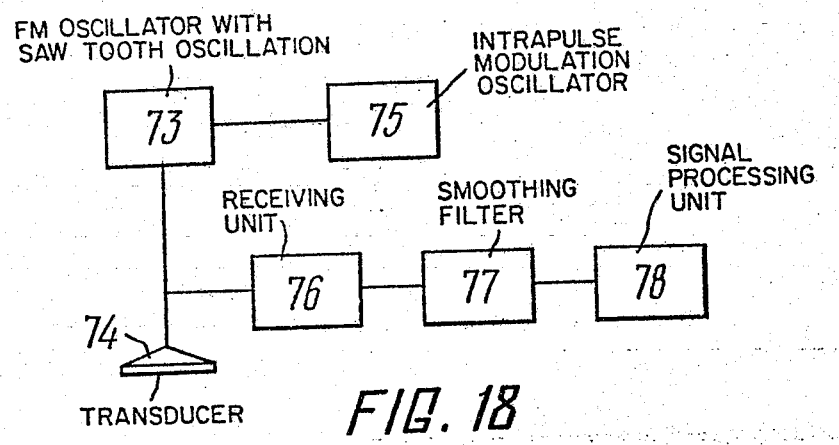
Figure 20:
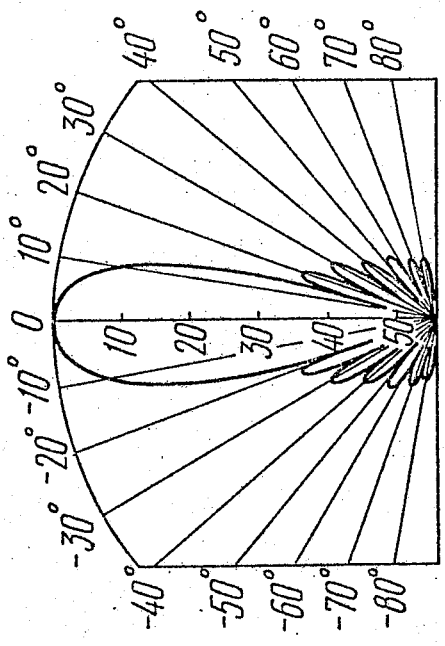
Figure 19:
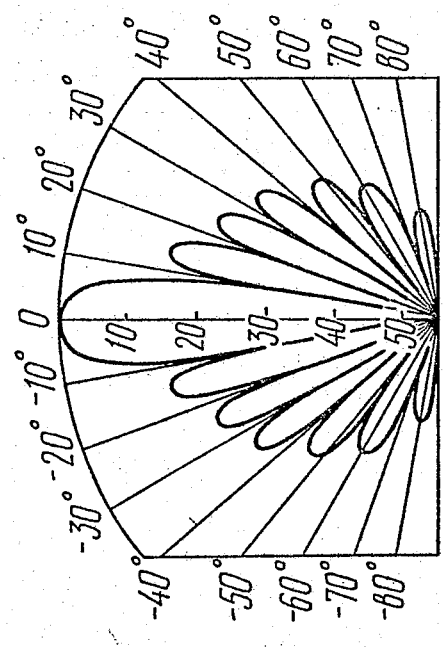

FIGS. 14a, b, c and d show a section taken along the line XIV—XIV of FIG. 13 for different versions of the wide-band ultrasonic transducer according to the invention;

FIGS. 15, 16 and 17 show sectional views of alternative embodiments of the testing head according to the invention;

FIG. 18 is a block diagram of a device to lower the side field level of the transducer in accordance with the invention;

FIG. 19 is a directivity diagram of the transducer prior to the suppression of the side field, according to the invention;

FIG. 20 is a directivity diagram of the transducer after the suppression of the side field, according to the invention.

All the wide-band ultrasonic transducers that are described below comprise a body of revolution having one flat end face surface face surface, its other end being profiled. The profile is made according to the following relationship:

$$h' = - p \cdot h \cdot k(f) \tag{1}$$

where
- $p$ is the radial coordinate of the transducer;
- $h$ is the thickness of the transducer, corresponding to the radial coordinate;
- $h'$ is the derivative of the thickness of the transducer with respect to the radial coordinate;
- $k(f)$ is the required frequency characteristics of the transducer.

Substituting into the equation 1 the required law of changing the frequency characteristic, we obtain an end face surface with a prescribed frequency characteristic.

Further in the text of the disclosure said transducers will be referred to as wide-band axisymmetric variable-thickness transducers.

It has been experimentally established that wide-band axisymmetric variable-thickness transducers emit and receive through annular portions with resonance thicknesses $h = C_1/2f$ corresponding to emission frequencies. $C_1$ is the speed of sound in the material of the transducer. In other words, an axisymmetric variable-thickness transducer is a set composed of a great number of narrow rings inserted one into another, each ring emitting at its own frequency. The change in the resonance thickness of each next ring is directly proportional to the required change in the frequency characteristic of the transducer. The expression 1 has been determined taking into account changes in the directivity diagram of each ring, depending upon the radius of the ring and the ultrasonic oscillation frequency.

Consider now examples of calculating the profile of an axisymmetric transducer's surface according to a preselected frequency characteristic.

1. Transducer with uniform frequency characteristic.

Figure 1A:
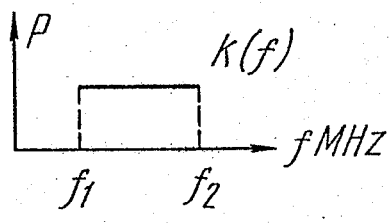

FIG. 1a shows a uniform conversion frequency within a frequency range from $f_1$ to $f_2$. In this case $k(f) = \text{const} = A$ (2), where $A$ is the proportionality factor.

Solving the equation 1, while taking into account 2, we obtain an analytical expression of the profile of the end face surface of the transducer, which is opposite the flat end face surface:

$$h = e^{-ap^2 + c} \qquad (3)$$

where $a$ and $c$ are constants determined by the operating frequency range of the transducer's pass band.

2. Transducer with a linearly rising characteristic.

Figure 1B:
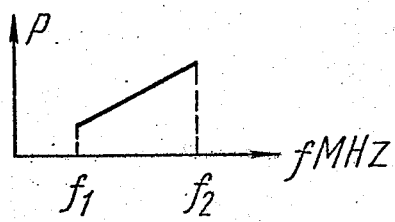

FIG. 1b shows a linearly rising frequency characteristic of a transducer in the frequency range between $f_1$ and $f_2$. Plotted on the abscissa is the frequency $f$; the amplitude B is plotted as ordinates. In this case $$K(f) = A \cdot f = B/h \qquad (4)$$

Solving the equation (1) for (4), we obtain an analytical expression for the profile of the transducer's surface $$h = c - a^1 p^2 \qquad (5)$$

3. Transducer with a frequency characteristic rising in proportion to the square of the freqency.

Figure 1E:
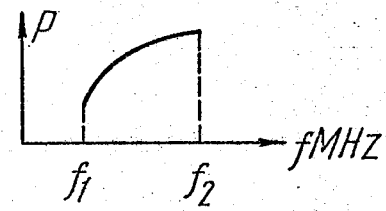
Figure 1C:
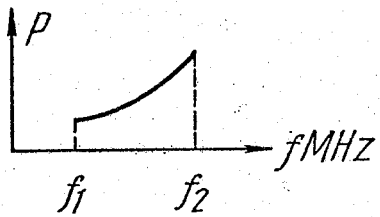

FIG. 1c shows a conversion frequency characteristic rising in proportion to the square of the frequency within a frequency range between $f_1$ and $f_2$. In this case $$K(f) = A \cdot f^2 = B/h^2 \qquad (6)$$

Solving the equation 1 for 6, we obtain an analytical expression for the profile of the transducer's surface:

$$h = c - ap \qquad (7)$$

4. Transducer with a frequency characteristic rising in proportion to the cube of the frequency.

Figure 1F:
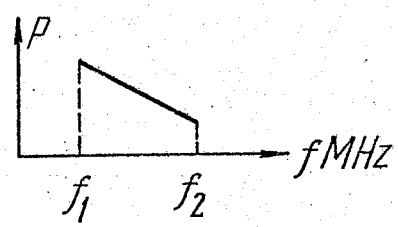
Figure 1D:
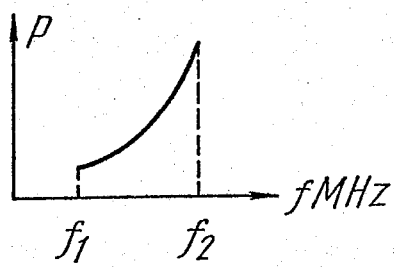

FIG. 1d shows a conversion frequency characteristic rising in proportion to the cube of the frequency in the frequency range between $f_1$ and $f_2$. In this case $$k(f) = Af^3 = B/h^3 \qquad (8)$$

Solving the equation (1) for (8), we obtain an analytical expression of the profile of the transducer's surface $$h = \sqrt[3]{c - ap^2} \qquad (9)$$

5. Transducer with a frequency characteristic rising in proportion to the natural logarithm of the frequency.

FIG. 1e shows a frequency characteristic rising in proportion to the natural logarithm of the frequency in the frequency range between $f_1$ and $f_2$. In this case $$k(f) = \ell n A f = \ell n (B/h) \qquad (10)$$

Solving the equation 1 for 10, we obtain an analytical expression of the profile of the transducer's surface $$h = \sqrt{e^{-ap^2}} \qquad (11)$$

6. Transducer with a linearly dropping frequency characteristic.

FIG. 1f shows a linearly dropping frequency characteristic within a frequency range from $f_1$ to $f_2$. In this case $$k(f) = A/f = B h \qquad (12)$$

Solving the equation (1) for (12) we obtain an analytical expression for the profile of the transducer's surface $$h = 1/(ap^2 - c) \qquad (13)$$

A wide-band ultrasonic transducer with a uniform frequency characteristic (FIG. 1a) comprises a body 1 of revolution (FIG. 2) made of a material having piezoelectric properties, and two electrodes 2 and 3 applied onto the end face surfaces of said body 1 of revolution. An end face surface 4 is profiled according to the relationship 3, and an end face surface 5 is flat.

Consider now a specific example of calculating the transducer in question.

The body 1 of revolution is made of lead zirconate-titanate.

The radius of the transducer $r = 10$ mm.

The operating frequency range is as follows:
$f_1 = 1.8$ mc
$f_2 = 10$ mc.

The maximum thickness at the edge of the transducer, corresponding to the emission of the frequency $f_1$ is as follows:

$$h_1 = c_1/2f_1 = 1 \,\mu\mu \qquad (14)$$

where $C_1$ is the speed of sound which in the above-mentioned material is equal to $3.6 \cdot 10^{-6}$ mm per second. The minimum thickness at the center of the transducer, corresponding to the emission of the frequency $f_2$, is $$h_2 = c_1/f_2 = 0,18 \,\mu\mu \qquad (15)$$

Substituting into the expression (3) the thickness values $h_1$ and $h_2$ we obtain the values of the constants $a$ and $c$:

at $h_2 = 0.18$ mm and $p = 0$, $C = -1.714$;
at $h_1 = 1$ mm and $p = r = 10$ mm, $a = 1.714 \cdot 10^{-2}$.
The expression (3) will now be as follows:

$$h = e^{1.714 \cdot 10^{-2} p^2 - 1.714} \qquad (16)$$

The profile of the given transducer's surface is close to a spherically concave one.

A transducer with a uniform frequency characteristic makes it possible to solve a number of problems in the field of ultrasonic measurements requiring the emission and reception of ultrasonic oscillations with a broad and uniform spectrum.

In a wide-band ultrasonic transducer with a linearly rising frequency characteristic (FIG. 1b) the profile of an end face surface 6 (FIG. 3) is made according to the relationship 5. An electrode 7 is applied onto said profiled surface 6.

Consider a specific example of calculating the transducer under review.

The body 1 of rotation is made of lead zirconate-titanate. The transducer's radius $r = 10$ mm; the operating frequency range is:
$f_1 = 1.8$ mc;
$f_2 = 10$ mc.

The maximum thickness at the center of the transducer, corresponding to the emission of the frequency $f_1$ is:

$$h_1 = c_1/2f_1 = 1 \mu\mu \qquad (17)$$

The minimum thickness at the edge of the transducer, corresponding to the emission of the frequency $f_2$, is:

$$h_2 = c_1/2f_2 = 0.18 \qquad (18)$$

Substituting into the expression 5 the values of the thicknesses $h_1$ and $h_2$, we obtain the values of the constants $a$ and $c$:
at $h_1 = 1$ mm and $\rho = 0$, $C = 1$;
at $h_2 = 0.18$ mm and $\rho = r = 10$ mm, $a = 8.2 \cdot 10^{-3}$.
The expression (1) will now be as follows:

$$h = 1 - 8.2 \cdot 10^{-3} \rho^2 \qquad (19)$$

The profile of the surface of this transducer is a portion of a convex sphere.

A transducer with a linearly rising frequency characteristic helps solve a number of problems pertaining to ultrasonic checking of materials, when it is necessary to compensate the frequency-dependent attenuation of a material being checked.

In an ultrasonic transducer whose frequency characteristic rises in proportion to the square of the frequency (FIG. 1c) the profile of an end face surface 8 is made according to the relationship 7, and an electrode 9 is applied onto said profiled surface 8.

Consider a specific example of calculating such a transducer.

The body 1 of revolution is made of lead zorconate-titanate. The transducer's radius $r = 10$ mm; the operating frequency range is:
$f_1 = 1.8$ mc;
$f_2 = 10$ mc.

The maximum thickness at the centre of the transducer, corresponding to the emission of the frequency $f_1$ is:

$$h_1 = C_1/2f_1 = 1 \mu\mu \qquad (20)$$

The minimum thickness at the center of the transducer, corresponding to the emission of the frequency $f_2$ is:

$$h = C_2/2f_2 = 0.18 \qquad (21)$$

Substituting into the expression (7) the values of the thicknesses $h_1$ and $h_2$, we obtain the values of the constants $a$ and $c$:
at $h_1 = 1$ mm and $\rho = 0$, $C = 1$;
at $h_2 = 0.18$ mm and $\rho = r = 10$ mm, $a = 8.2 \cdot 10^{-2}$.
The expression (7) will now be as follows:

$$h = 1 - 8.2 \cdot 10^{-2} \rho \qquad (22)$$

The surface profile of this transducer has the form of a conical surface.

Such a transducer helps solve a number of problems pertaining to ultrasonic checking of materials, when it is necessary to compensate increased frequency-dependent attenuation, for example, in steel, within a wide frequency range.

Figure 5:
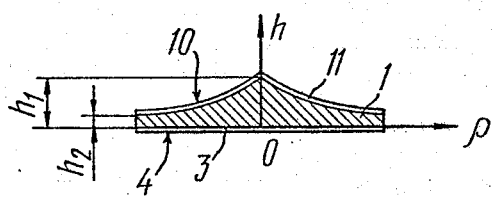
FIG. 5 shows a wide-band ultrasonic transducer with a frequency characteristic which rises in proportion to the cube of the frequency, in accordance with the invention.

In a wide-band ultrasonic transducer whose frequency characteristic rises in proportion to the cube of the frequency (FIG. 1d), the profile of an end face surface 10 (FIG. 5) is made according to the relationship 9, and an electrode 11 is applied onto said profiled surface 10.

Figure 6:
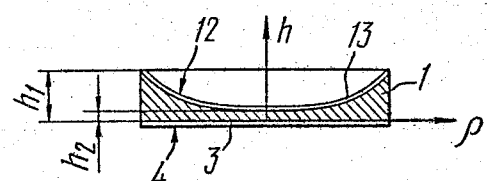
FIG. 6 shows a wide-band ultrasonic transducer with a frequency characteristic rising in proportion to the natural logarithm of the frequency, in accordance with the invention.

In a wide-band ultrasonic transducer whose frequency characteristic rises in proportion to the natural logarithm of the frequency (FIG. 1e), the profile of an end face surface 12 (FIG. 6) is made according to the relationship 11, and an electrode 13 is applied onto said profiled surface 12.

Figure 7:
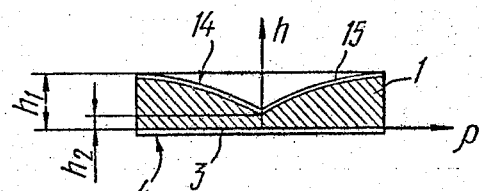
FIG. 7 shows a wide-band ultrasonic transducer with a linearly dropping frequency characteristic in accordance with the invention.
Figure 4:
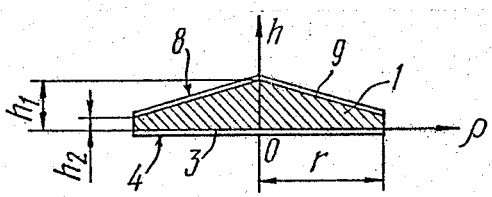
FIG. 4 shows a wide-band ultrasonic transducer with a frequency characteristic which rises in proportion to the square of the frequency, in accordance with the invention.

In a wide-band ultrasonic transducer with a linearly dropping frequency characteristic (FIG. 1f) the profile of an end face surface 14 (FIG. 7) is made according to the relationship 13, and an electrode 15 is applied onto said profiled surface 14.

It should be pointed out that for axisymmetric variable-thickness transducers constructed in accordance with some or other of the above embodiments and ensuring a required conversion frequency characteristic it is altogether unnecessary that one of the surfaces be flat. This surface may be curvilinear. Yet in order to avoid changes in the conversion frequency characteristic, it is necessary to meet the condition of the law of the change in the transducer's thickness with respect to the radius throughout the operating frequency range.

In this case the expressions for the surface profile of the transducer reflect not the profile, but the law of the change in the transducer's thickness with respect to its radius.

Figure 8:
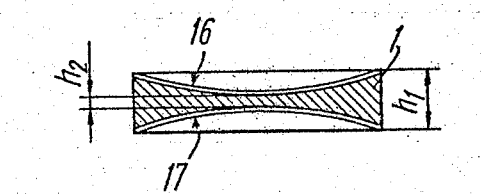
FIGS. 8 and 9 show alternative embodiments of the wide-band ultrasonic transducer with a uniform frequency characteristic, according to the invention.

FIG. 8 shows a transducer with a uniform frequency characteristic; in this case the change in the thickness with respect to the radius is reflected by the expression 3.

In this transducer both end face surfaces 16 and 17 of the body 1 of revolution have identical profiles. The thicknesses $h_1$ and $h_2$ are found as in the case of the transducer with a uniform frequency characteristic shown in FIG. 2.

Figure 9:
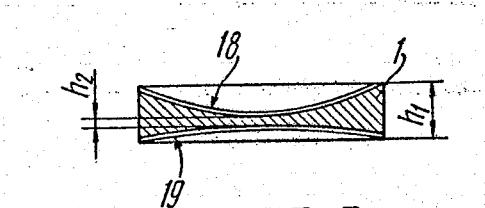

FIG. 9 shows a transducer with a uniform frequency characteristic in whose case the change of the thickness with respect to the radius is also defined by the expression 3. Yet here the profiles of end face surfaces 18 and 19 are different, the curvature of the surface 18 being less than that of the surface 19.

Figure 10:
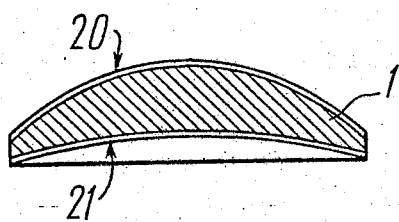
FIG. 10 shows an alternative embodiment of the wide-band ultrasonic transducer with a linearly rising frequency characteristic, according to the invention.

FIG. 10 shows a transducer with a linearly rising frequency characteristic. In this case the change in the thickness with respect to the radius is defined by the expression 5. Note, however, that a surface 20 is convex, whereas a surface 21 is concave.

Figure 11:
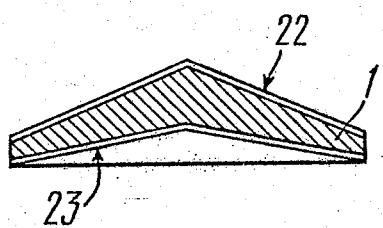
FIG. 11 shows an alternative embodiment of the wide-band ultrasonic transducer with a frequency characteristic rising in proportion to the square of the frequency, according to the invention.

FIG. 11 shows a transducer whose characteristic rises in proportion to the square of the frequency. For this transducer the law of the change in the thickness with respect to the radius is defined by the expression 7. The profile of a surface 22 is conically convex, whereas that of a surface 23 is conically concave.

Figure 2:
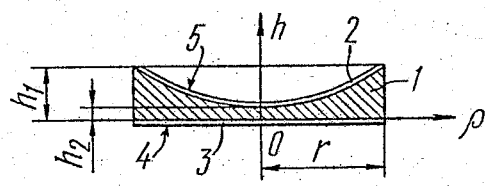
FIG. 2 shows a wide-band ultrasonic transducer with a uniform frequency characteristic according to the invention.
Figure 3:
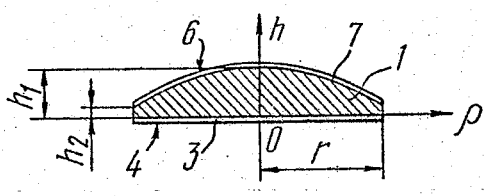
FIG. 3 shows a wide-band ultrasonic transducer with a linearly rising frequency characteristic according to the invention.
Figure 12:
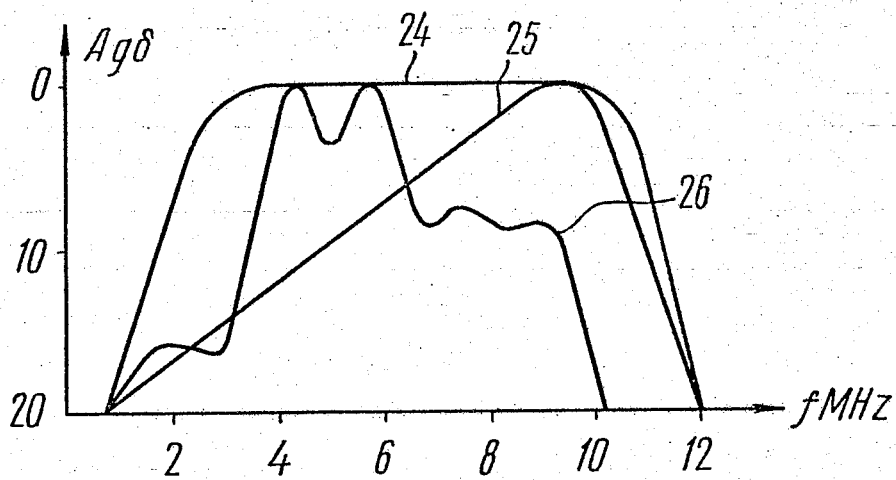
FIG. 12 represents experimental frequency characteristics of the wide-band ultrasonic transducer according to the invention.

FIG. 12 represents experimentally measured frequency characteristics of a transducer with a uniform frequency characteristic 24 similar to that of FIG. 2 with a linearly rising characteristic 25 and similar to that of FIG. 3. For comparison, FIG. 12 also represents a frequency characteristic 26 of a mechanically and electrically damped plane-parallel transducer with a resonance frequency $f_a = 5$ mc.

The transducer under review has the following parameters: $r = 10$ mm, $h_1 = 1$ mm, and $h_2 = 0.18$ mm.

The curves of FIG. 12 graphically indicate that the actual frequency characteristics of the wide-band axisymmetric transducers of variable thickness correspond well to preselected frequency characteristics, and that they have a more monotone form and a greater operating frequency range that plane-parallel transducers.

As it has been noted above, axisymmetric variable-thickness transducers emit and receive by means of narrow rings thereof. Experiments show that for such transducers the Fresnel region is considerably decreased. The limits of the Fresnel region for a transducer emitting and receiving by means of a narrow ring are determined by the following expression:

$$Z = (\rho \cdot \Delta a)/\lambda \qquad (23)$$

where
$\Delta Q$ is the ring width;
$\rho$ is the ring radius; and
$\lambda$ is the wavelength of ultrasound in the medium.

It is clear from the expression 23 that the narrower the ring, the lesser the Fresnel region; it is also clear that the greater the difference in the thicknesses of an axisymmetric variable-thickness transducer, the lesser the Fresnel region. For example, for a plane-parallel transducer with a radius $r = 6$ mm, which emits into water at a frequency of 2 mc, $Z = 48$ mm; whereas, for a conically convex transducer with thicknesses $h_1 = 1$ mm and $h_2 = 0.25$ mm, $Z = 2.01$ mm.

FIG. 13 shows a general view of an ultrasonic testing head incorporating wide-band axisymmetric variable-thickness transducers.

This ultrasonic testing head comprises a housing 27 (FIG. 13), wherein there are arranged a damper 28, a transducer 29, and a protector 30 (FIG. 14a). The housing 27 is provided with a plug connector 31. The transducer 29 has a flat end face surface 32 and a profiled end face surface 33 which in the present case is concave. The testing head is connected to a flaw detector by means of the plug connector 31. The transducer 29 is coupled with its flat end face surface 32 to the damper 28. Arranged on the side of the profiled end face surface 33 of the transducer 29 is the protector 30. One of its surfaces is flat, whereas the other, facing the transducer, is congruent with the profiled end face surface 33 of the transducer. This design of the testing head makes it possible to stabilize the amplitude of emitted and received ultrasonic oscillations with variations in the thickness of the contact fluid layer between the testing head and an article being checked, i.e. to stabilize the acoustic contact between the testing head and the surface of the article. In addition, such a design of the testing head makes it possible to stabilize the amplitude-frequency distribution of ultrasonic oscillation components in the spectrum during the transition through the contact layer.

The physical explanation of the increased stability of the acoustic contact is the fact that the protector is variable in thickness and is not resonant at any frequency of the ultrasonic oscillation spectrum. This reduces the effects of variations in the thickness of the contact fluid layer upon the frequency characteristic of the transducer, so that the amplitude of ultrasonic oscillations remains constant during the transition through the contact layer.

$d$ has been experimentally established, for example, that for a testing head with a plane-parallel transducer having a diameter $d = 20$ mm and tuned to a frequency of 2 mc, and with a plane-parallel protector, a change in the contact layer thickness from 0.1 mm to 0.4 mm changes the amplitude of the received signal by 25 db; meanwhile, for the testing head of FIG. 14a, a difference in the thicknesses from $h_1 = 1$ mm to $h_2 = 0.25$ only accounts for a change by 3 db.

Figure 14B:
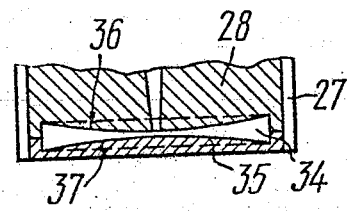

FIG. 14b shows an alternative embodiment of the testing head which incorporates a transducer with two profiled end face surfaces similar to the one of FIG. 8. The testing head comprises a housing 27 wherein there are arranged a damper 28, a transducer 34 and a protector 35. Both end face surfaces 36 and 37 of the transducer are profiled. In this case the surface of the damper 28 has a reversed profile with respect to the surface 36 of the transducer 34. One of the surfaces of the protector 35 is flat, whereas the other, facing the transducer 34, is profiled and congruent with the surface 37 of the transducer 34.

Figure 14C:
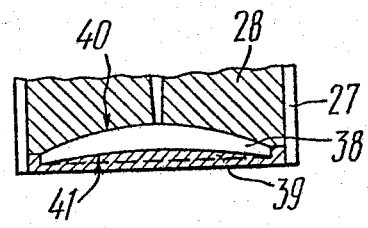

FIG. 14c shows another alternative embodiment of the testing head which incorporates a transducer similar to that of FIG. 9. The testing head comprises a housing 27 wherein there are arranged a damper 28, a transducer 38 and a protector 39. A surface 40 of the transducer 38 is convex, whereas its surface 41, facing the protector 39, is concave.

Figure 14D:
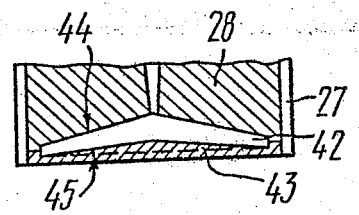

FIG. 14d shows still another embodiment of the testing head which incorporates a transducer similar to the one of FIG. 10. The testing head comprises a housing 27 wherein there are arranged a damper 28, a transducer 42 and a protector 43. A surface 44 of the transducer 42 is conically convex, whereas a surface 45, facing the protector 43, is conically concave.

All the foregoing embodiments of the testing head feature an increased acoustic contact stability. The function of the transducer in these testing heads may be performed by a wide-band axisymmetric variable-thickness transducer of any shape. But one condition must necessarily be met: the surface of the transducer, facing the protector, must be curvilinear, whereas the protector and transducer must combine to form a plane-parallel disc.

FIG. 15 shows an embodiment of a testing head intended for an ultrasonic flaw detector having an increased acoustic contact stability. The testing head comprises a housing 46 wherein there are arranged a contact ring 47, a transducer 48, a protector 49 and a damper 50. Mounted on the outer surface of the housing 46, by means of a threaded connection, is a bushing 51 at whose base there is a supporting ring 52. The bushing 51 is secured to the housing 46 by means of a locknut 53. A handle 54 has a bushing 55 to hold the housing 46. The flaw detector and the transducer are electrically interconnected with the aid of a plug connector 56, contacts 57 and 58 and the contact ring 47. The bushing 51 has a pipe connection 59 for the supply of contact fluid. The associations and designs of the damper 50, the transducer 48 and the protector 49 are similar to those of FIG. 14a. There may be two operating positions of the testing head, a contact position and a gap position. In the latter position the bushing 51 is moved out so that between the plane of the supporting ring 52 and the outer surface of the protector 49 there is formed a gap of a desired width. Instead of the supporting ring 52 use may be made of supporting balls arranged along the perimeter of the end face surface of the bushing 51.

FIG. 16 shows a testing head provided with a device for changing ultrasonic oscillation frequency. The testing head under review comprises a housing 60, a damper 61, a protector 62, a wide-band axisymmetric variable-thickness transducer 63, a ferromagnetic core 64 having an inductance coil 65 wound around it, said inductance coil being connected in parallel with the transducer 63 and forming an oscillatory circuit therewith, and a permanent magnet 66 mounted on a base 67. Mounted on the housing 60 is a bushing 68 having an internal helical groove, which bushing 68 is coupled to the base 67 by means of a pin 69. The testing head is connected to a flaw detector by means of a plug connector 70. On the end face surface of the bushing 68 there are frequency scale divisions 71.

As the bushing 68 is turned, the permanent magnet 66 is displaced in the gap of the core 64. This changes the magnetic flux through the core 64 and the inductance of the inductance coil 65, which, in turn, alters the ultrasonic oscillation frequency. Having graduated the scale on the bushing 68 in terms of frequency, one may easily and rapidly switch from one frequency to another. The associations of the damper 61, the protector 62 and the transducer 63 are similar to those of FIG. 14.

FIG. 17 shows a sectional view of an inclined testing head whose design is similar to that of the head shown in FIG. 16, the only difference being that in the former a prism 72 is employed instead of the protector 62.

The current trend in designing ultrasonic flaw detectors and thickness gauges is marked by attempts to produce instruments provided with a wide-band receiving amplifier. In such instruments the switching from one frequency to another is only made possible by changing the frequency of the testing head.

It should be pointed out that testing heads of the above-mentioned designs make it possible to form very short ultrasonic pulses with a duration of 1 to 2 periods. This reduces the shadow zone and raises the resolving power and accuracy of measurements.

Consider now a device for suppressing the side field of a transducer.

Controlled suppression of the side field of a transducer is based on changing the aperture of the transducer with time, which changes the angular position of the minor lobes of the transducer's directivity diagram. In the process of filtering a signal received by the transducer there is formed a total directivity diagram which is the result of adding the minor lobes while taking into account the phase thereof. Such signal processing makes it possible to substantially reduce the side field level and completely suppress the signal at places where the added lobes are in antiphase.

The aperture of a transducer can be changed in different ways, in particular, by predetermined commutation of peripheral zones of the transducer and modulating the ultrasonic oscillation frequency.

The directivity diagram of a transducer with an aperture that changes with time may be represented as follows:

$$F(Q,t) = \int_{-T/2}^{T/2} \int_{-e(t)/2}^{e(t)/2} P(x) \cdot \exp\left[\frac{i2\pi fx}{C}\sin Q\right] dx\, dt \quad (24)$$

where
$F(Q, t)$ is the directivity diagram;
$Q$ is the angle in the directivity diagram;
$T$ is the modulation period of the aperture size;
$l(t)$ is the aperture size;
$P(x)$ is the amplitude distribution in the aperture;
$f$ is the signal frequency; and
$C$ is the speed of sound.

Suppose one changes the size of the aperture with time so that in the period of time $-(T/2) < t < 0$ emission is carried out by the whole of the aperture and that in the moment of time $0 < t < (T/2)$ part of the aperture along the edges of the transducer is out of action.

In this case the mean voltage value during the time T is expressed as follows:

$$F(Q) = \tfrac{1}{2}\int_{-l/2}^{l/2} P(x)\exp\left[\frac{i2\pi fx}{C}\sin Q\right] dx + \tfrac{1}{2}\int_{-l_1/2}^{l_1/2} P(x)\exp\left[\frac{i2\pi fx}{C}\sin Q\right] dx \quad (25)$$

where $l - l_1 = \Delta l$ is the part of the aperture out of action.

Let us assume that the amplitude distribution over the surface of the transducer is uniform. Then the resultant directivity diagram will be represented as follows:

$$F(Q) = \frac{\sin\left[\frac{l+l_1}{2}\frac{\pi}{\lambda}(\sin Q)\right] \cdot \cos\left[\frac{l-l_1}{2}\frac{\pi}{\lambda}(\sin Q)\right]}{\frac{l+l_1}{2}\frac{\pi}{\lambda}(\sin Q)} \quad (26)$$

It is seen from the above expression that in its mean value the directivity diagram has this factor:

$$m = \cos\left[\frac{l-l_1}{2}\frac{\pi}{\lambda}\sin Q\right] \quad (27)$$

which factor determines an additional minimum in the directivity diagram.

By varying the depth of the change with time of the aperture size $(1 - l_1)$, it is possible to change the location of the lobe minimization zone in the directivity diagram of the transducer.

It can be shown that the presence of a controlled lobe suppression zone has small effect upon the major lobe of the directivity diagram.

Determine now the ratio between the beam width of a detector with a controlled lobe suppression system and that of a detector operating without suppressing the minor lobes.

$$\Delta Q_n = 0.886 \frac{\lambda}{e} \quad (28)$$

$$\Delta Q = 0.886 \frac{\lambda}{\frac{l-l_1}{2}} \quad (29)$$

$$\frac{\Delta Q_n}{\Delta Q} = 1 + \frac{l-l_1}{2l} \quad (30)$$

Since normally $1 - l_1 \ll 1$, it is inferred that $(\Delta Q_0/\Delta Q) \approx 1$.

Thus, controlled suppression of minor lobes has no significant effect upon the width of the main peak of the directivity diagram.

In the case of changing the acting aperture size of a transducer by modulating the frequency according to the sinusoidal law, the expression 24 for the resultant directivity diagram of the transducer will be as follows:

$$F(Q) = \frac{\sin\left[\frac{\pi r}{2C} f_i \sin Q\right]}{\frac{\pi r}{2C} f_i \sin Q} \cdot J_0\left[\frac{\pi r}{2C} \cdot \frac{\Delta f_i}{2} \sin Q\right] \quad (31)$$

where
- $r$ is the radius of the transducer;
- $f_i$ is the present-moment value of ultrasonic oscillation frequency;
- $\Delta f_i$ is the magnitude of the frequency deviation; and
- $J_0$ is the Bessel function of the zero order.

The directivity diagram acquires a factor $$m = J_0\left[\frac{\pi r}{2C} \cdot \frac{\Delta f_i}{2} \sin Q\right] \quad (32)$$

which accounts for additional substantial lowering of the level of the transducer's minor lobes.

FIG. 18 shows a block diagram of a device to lower the level of the minor lobes of a transducer intended for ultrasonic flaw detection and determining types of flaws.

The device comprises an oscillator 73 of probing frequency-modulated oscillations, whose pulse filling frequency changes from pulse to pulse according to the sawtooth law, a wide-band axisymmetric variable-thickness transducer 74 connected to the probing pulse oscillator 73, an intrapulse modulation oscillator 75 connected to the oscillator 73, a wide-band receiving unit 76 connected to the transducer 74, a smoothing filter 77, and a signal processing unit 78.

The device operates as follows.

The oscillator 73 generates a sequence of radiopulses with filling frequencies $f_1, f_2, \ldots f_n$; the oscillator 75 generates intrapulse modulation frequency voltage with a predetermined law of frequency modulation, i.e. ensures frequency deviation by $\Delta f_i$. Thus, the total sequence of radiopulses applied to the transducer 74 will be expressed as $f_1 = \Delta f_1, f_2 = \Delta f_2, \ldots f_n = \Delta f_n$.

During periods of time between emissions of probing pulses the transducer 74 receives signals reflected from flaws. Noise signals are amplified and gated by the receiving unit 76. The filter 77 averages the noise signals with time, lowers the overall level of the minor lobes and fully suppresses them in the zone where the minor lobes are in antiphase. By changing the depth of intrapulse frequency modulation, it is possible to change the location of the zone of complete suppression of side emission; by changing the law of intrapulse modulation, it is possible to change the width of the suppression zone.

Thus, with the sinusoidal law of intrapulse modulation, the suppressions involves a greater part of minor lobes. The unit 78 carried out signal processing in ac-cordance with specific tasks. For example, in the course of determining the size and nature of flaws, the unit 78 carries out spectral analysis of signals reflected from flaws and compares the results to reference spectra.

FIGS. 19 and 20 show, by way of an example, directivity diagrams of a transducer similar to the one of FIG. 2, with a radius $r = 6$ and thicknesses $h_1 = 1$ mm. and $h_2 = 0.25$ mm, measured prior to and after suppression of side emission (FIGS. 19 and 20, respectively), with the sinusoidal law of intrapulse modulation. The ultrasonic oscillation frequency $f = 2$ mc. A comparison of the directivity diagrams shows that the aid of the foregoing device it is possible to lower the level of the side field by 25 db, which is practically sufficient to rule out noise due to the minor lobes.

The proposed devices for suppressing side fields may also be used with plane-parallel transducers whose pass bands allow a necessary frequency deviation.

For narrow-band transducers side fields can be suppressed by way of periodically bringing out of action the peripheral zones of a transducer, which peripheral zones are connected to the central zone with the aid of a switch in accordance with a predetermined law.

What is claimed is:

1. A wide-band ultrasonic transducer comprising: a body of revolution; at least two electrodes connected to said body of revolution; said body of revolution being made of a material possessing piezoelectric properties and having one flat end face surface, its other end face surface, opposite said flat end face surface, being profiled; the profile of said profiled end face surface of said body of revolution being made in accordance with the following relationships:

$$h' = -p \cdot h \cdot k(f)$$

where
- $p$ is the radial coordinate;
- $h$ is the thickness of said transducer, corresponding to the radial coordinate;
- $k(f)$ is the frequency characteristic of said transducer;
- $h'$ is the derivative of the thickness $h$ of the transducer with respect to the radial coordinate;

said electrodes being applied onto said flat end face surface and said profiled end face surface of said body of revolution.

2. A wide-band ultrasonic transducer having a uniform conversion frequency characteristic within the operating frequency range and comprising: a body of revolution; at least two electrodes connected to said body of revolution; said body of revolution being made of a material possessing piezoelectric properties and having one flat end face surface, its other end face surface, opposite said flat end face surface, being profiled, the profile of said profiled end face surface being made according to the relationship:

$$h = c \cdot e^{-a p^2}$$

where $a$ and $c$ are constant values determined by the operating frequency range; $p$ is the radial coordinate and $h$ is the thickness of the transducer corresponding to the radial coordinate, said electrodes being applied onto said flat end face surface and said profile end face surface of said body of revolution.

3. A wide-band ultrasonic transducer having a linearly rising frequency characteristic within the operating frequency range and comprising: a body of revolution; at least two electrodes connected to said body of revolution; said body of revolution being made of a material possessing piezo-electric properties and having one flat end face surface, its other end face surface, opposite said flat end face surface, being profiled, the profile of said profiled end face surface being made in accordance with the following relationship:

$$h = c - a \cdot p^2,$$

wherein $a$ and $c$ are constants determined by the operating frequency range, $\rho$ is the radial coordinate, and $h$ is the thickness of said transducer corresponding to the radial coordinate, said electrodes being applied onto said flat end face surface and said profiled end face surface of said body of revolution.

4. A wide-band ultrasonic transducer having a conversion frequency characteristic rising in proportion to the square of the frequency within the operating frequency range and comprising: a body of revolution; at least two electrodes connected to said body of revolution; said body of revolution being made of a material possessing piezoelectric properties and having one flat end face surface, its other end face surface, opposite said flat end face surface, being profiled, the profile of said profiled end face surface being made according to the relationship:

$$h = c - a \cdot p$$

where $a$ and $c$ are constants determined by the operating frequency range; $\rho$ is the radial coordinate, and $h$ is the thickness of said transducer corresponding to the radial coordinate, said electrodes being applied onto said flat end face surface and said profiled end face surface of said body of revolution.

5. A probe for nodestructive ultrasonic checking, comprising: a housing; a damper arranged in said housing; a wide-band ultrasonic transducer connected to said damper, a protector connected to said wide-band ultrasonic transducer; said wide-band ultrasonic transducer comprising a body of revolution, said body of revolution being made of a material possessing piezoelectric properties and having one flat end face surface, its other end face surface, opposite said flat end face surface, being profiled, the profile of said profiled end face surface being made according to the following relationship:

$$h' = - p \cdot h \cdot k (f)$$

where
$\rho$ is the radial coordinate;
$h$ is the thickness of said body of revolution, corresponding to the radial coordinate;
$k(f)$ is the frequency characteristic of the transducer;
$h'$ is the derivative of the thickness $h$ of the body of revolution with respect to the radial coordinate $\rho$;
said electrodes being applied onto said flat end face surface and said profiled end face surface of said body of revolution; said wide-band ultrasonic transducer facing said damper with its flat end face surface; said protector having a surface facing said wide-band ultrasonic transducer to which is congruent with the latter's profiled end face surface.

6. A probe as claimed in claim 5, comprising: a ferromagnetic core with an inductance coil wound therearound, said coil forming, together with said wide-band ultrasonic transducer, an oscillatory circuit; a permanent magnet installed in the gap of said ferromagnetic core and adapted for axial movement.

7. A probe for nondestructive ultrasonic checking, comprising: a housing; a damper arranged in said housing; a wide-band ultrasonic transducer connected to said damper; a protector connected to said wide-band ultrasonic transducer; said wide-band ultrasonic transducer having a uniform frequency characteristic within the operating frequency range, comprising: a body of revolution, at least two electrodes connected to said body of revolution, said body of revolution being made of a material possessing piezoelectric properties and having one flat end surface, its other end face surface, opposite said flat end face surface, being profiled, the profile of said profiled end face surface being made according to the following relationship:

$$h = e^{-a p^2} + c$$

where $a$ and $c$ are constant values determined by the operating frequency range; $\rho$ is the radial coordinate, and $h$ is the thickness of the transducer corresponding to the radial coordinate, said electrodes being applied onto said flat end surface and said profiled end face surface of said body of revolution; said wide-band ultrasonic transducer facing said damper with its flat end face surface; said protector having a surface, facing said wide-band ultrasonic transducer, which is congruent with the latter's profiled end face surface.

8. A probe as claimed in claim 7, comprising: a ferromagnetic core having an inductance coil wound therearound, said coil forming, together with said wide-band ultrasonic transducer, an oscillatory circuit; a permanent magnet installed in the gap of said ferromagnetic core and adapted for axial movement.

9. A probe for nondestructive ultrasonic checking, comprising: a housing; a damper arranged in said housing; a wide-band ultrasonic transducer connected to said damper; a protector connected to said wide-band ultrasonic transducer; said wide-band ultrasonic transducer having a linearly rising frequency characteristic within the operating frequency range and comprising: a body of revolution, at least two electrodes connected to said body of revolution, said body of revolution being made of a material possessing piezoelectric properties and having one flat end face surface, its other end face surface, opposite said flat end face surface, being profiled, the profile of said profiled end face surface being made according to the following relationship:

$$h = c - a \cdot p^2$$

where $a$ and $c$ are constants determined by the operating frequency range; $\rho$ is the radial coordinate; and $h$ is the thickness of said transducer corresponding to the radial coordinate, said electrodes being applied onto said flat end surface and said profiled end face surface of said body of revolution; said wide-band ultrasonic transducer facing said damper with its flat end face surface; said protector having a surface facing said wide-band ultrasonic transducer which is congruent with the latter's profiled end face surface.

10. A probe as claimed in claim 9, comprising: a ferromagnetic core having an inductance coil wound therearound, said coil forming, together with said wide-band ultrasonic transducer, an oscillatory circuit; a permanent magnet installed in the gap of said ferromagnetic core and adapted for axial movement.

11. A probe for nondestructive ultrasonic checking, comprising: a housing; a damper arranged in said housing; a wide-band ultrasonic transducer connected to said damper; a protector connected to said wide-band ultrasonic transducer; said wide-band ultrasonic transducer having a conversion frequency within the operating frequency range and comprising: a body of revolution, at least two electrodes connected to said body of revolution, said body of revolution being made of a material possessing piezoelectric properties and having one flat end face surface, its other end face surface, opposite said flat end face surface, being profiled, the profile of said profiled end face surface being made in accordance with the following relationship:

$$h = c - a \cdot \rho$$

wherein $a$ and $c$ are constants determined by the operating frequency range, $\rho$ is the radial coordinate, and $h$ is the thickness of said transducer corresponding to the radial coordinate, said electrodes being applied onto said flat end surface and said profiled end face surface of said body of revolution; said wide-band ultrasonic transducer facing said damper with its flat end surface; said protector having a surface facing said wide-band ultrasonic transducer which is congruent with the latter's profiled end face surface.

12. A probe as claimed in claim 11, comprising: a ferromagnetic core having an inductance coil wound therearound, said coil forming, together with said wide-band ultrasonic transducer, an oscillatory circuit; a permanent magnet installed in the gap of said ferromagnetic core and adapted for axial movement.

13. A device for nondestructive ultrasonic checking, comprising: an oscillator of probing frequency-modulated oscillations; a wide-band ultrasonic transducer connected to an output of said oscillator of probing frequency-modulated oscillations; a wide-band receiving unit connected to said wide-band ultrasonic transducer; an intrapulse frequency modulation oscillator connected to said wide-band ultrasonic transducer; a signal processing unit connected to said wide-band receiving unit; a smoothing filter placed between said wide-band ultrasonic transducer and said signal processing unit; and wide-band ultrasonic transducer comprising a body of revolution, body of revolution being made of a meterial possessing piezoelectric properties and having one flat end face surface, its other end face surface, opposite said flat end face surface, being profiled, the profile of said profiled end face surface being made in accordance with the following relationship:

$$h' = -\rho \cdot h \cdot k(t).$$

where
$\rho$ is the radial coordinate;
$h$ is the thickness of said body of revolution, corresponding to the radial coordinate;
$k(f)$ is the frequency characteristic of the transducer;
$h'$ is a derivative of the thickness of $h$ of the body of revolution with respect to the radial coordinate $\rho$; said electrodes being applied onto said flat end face surface and said profiled end face surface of said body of revolution.

14. A device for nondestructive checking, comprising: an oscillator of probing frequency-modulated oscillations; a wide-band ultrasonic transducer connected to an output of said oscillator of probing frequency-modulated oscillations; a wide-band receiving unit connected to said wide-band ultrasonic transducer; an intrapulse frequency modulation oscillator connected to said wide-band ultrasonic transducer; a signal processing unit connected to said wide-band receiving unit; a smoothing filter placed between said wide-band ultrasonic transducer and said signal processing unit; said wide-band ultrasonic transducer having a uniform conversion frequency characteristic within the operating frequency range and comprising a body of revolution, at least two electrodes connected to said body of revolution, said body of revolution being made of a material possessing piezoelectric properties and having one flat end face surface, its other end face surface, opposite said flat end face surface, being profiled, the profile of said profiled end face surface being made in accordance with the following relationship:

$$h = e^{-a \cdot \rho^2} + c,$$

where $a$ and $c$ are constant values determined by the operating frequency range; $\rho$ is the radial coordinate and $h$ is the thickness of the transducer corresponding to the radial coordinate, said electrodes being applied into said flat end surface and said profiled end face surface of said body of revolution.

15. A device for wide-band ultrasonic checking, comprising: an oscillator of probing frequency-modulated oscillations; a wide-band ultrasonic transducer connected to an output of said oscillator of probing frequency-modulated oscillations; a wide-band receiving unit connected to said wide-band ultrasonic transducer; an intrapulse frequency modulation oscillator connected to said wide-band ultrasonic transducer; a signal processing unit connected to said wide-band receiving unit; a smoothing filter placed between said wide-band ultrasonic transducer and said signal processing unit; said wide-band ultrasonic transducer having a linearly rising frequency characteristic within the operating frequency range and comprising a body of revolution, at least two electrodes connected to said body of revolution, said body of revolution being made of a material possessing piezoelectric properties and having one flat end face surface, its other end face surface, opposite said flat end face surface, being profiled, the profile of said profiled end face surface being made in accordance with the following relationship:

$$h = c - a \cdot \rho^2$$

wherein $a$ and $c$ are constants determined by the operating frequency range, $\rho$ is the radial coordinate, and $h$ is the thickness of said transducer corresponding to the radial coordinate, said electrodes being applied onto said flat end face surface and said profiled end face surface of said body of revolution.

16. A device for nondestructive ultrasonic checking, comprising: an oscillator of probing frequency-modulated oscillations; a wide band-ultrasonic transducer connected to an output of said oscillator of probing frequency-modulated oscillations; a wide-band receiving unit connected to said wide-band ultrasonic transducer; an intrapulse frequency modulation oscillator connected to said wide-band ultrasonic transducer;

a signal processing unit connected to said wide-band receiving unit; a smoothing filter placed between said wide-band ultrasonic transducer and said signal processing unit; said wide-band ultrasonic transducer having a conversion frequency characteristic rising in proportion to the square of the frequency within the operating frequency range and comprising a body of revolution, at least two electrodes connected to said body of revolution, said body of revolution being made of a material possessing piezoelectric properties and having one flat end surface, its other end face surface, opposite said flat end face surface, being profiled, the profile of said profiled end face surface being made in accordance with the following relationship:

$$h = c - a \cdot \rho;$$

wherein $a$ and $c$ are constants determined by the operating frequency range, $\rho$ is the radial coordinate, and $h$ is the thickness of said transducer corresponding to the radial coordinate, said electrodes being applied onto said flat end face surface and said profiled end face body of of said body revolution.

* * * * *